United States Patent [19]

Zetter

[11] 4,359,527

[45] Nov. 16, 1982

[54] CANCER DIAGNOSTIC ASSAY

[75] Inventor: Bruce R. Zetter, Boston, Mass.

[73] Assignee: The Children's Hospital Medical Center, Boston, Mass.

[21] Appl. No.: 201,293

[22] Filed: Oct. 27, 1980

[51] Int. Cl.³ .............................................. C12Q 1/29
[52] U.S. Cl. ................................................... 435/29
[58] Field of Search ........................................ 435/29

[56] References Cited

PUBLICATIONS

Albrecht-Buehler, (1977), *J. Cell Biol.*, 72, 595.
Ali et al., (1978), *Cell*, 14, 439.

*Primary Examiner*—Robert J. Warden

[57] ABSTRACT

In vitro cancer diagnostic assay comprising providing a substratum coated with a layer of visible particles susceptible to ingestion by capillary endothelial cells, plating such cells onto the substratum, allowing the cells to adhere, incubating the cells with a test sample, measuring the area of the visible particle-depleted phagokinetic track left by at least one of the cells, and comparing that area to the track area left by a control cell, a comparatively larger test track area indicating the presence in the test sample of a factor associated with cancer cells.

6 Claims, 6 Drawing Figures

CANCER DIAGNOSTIC ASSAY

The invention described herein was made in the course of work under a grant from the Department of Health, Education and Welfare.

This invention relates to cancer diagnostic assays.

Cancer screening tests are of two basic types: invasive and non-invasive. Taking bladder cancer as an example, the primary invasive test used is the endoscopic examination, which is usually repeated every three months for patients with histories of non-invasive carcinoma of the bladder, and may also be performed periodically on members of high-risk groups such as dye and paint factory workers.

Among non-invasive diagnostic tests, uniary cytology is the most reliable currently in use. The accuracy of urinary cytologies is usually between 60% and 80%, but can be considerably less accurate in the detection of low-grade, low-stage disease. Furthermore, the use of intravesical antineoplastic drugs increases the number of false positive results for this test.

The measurement of other diagonistic markers in the urine, e.g., LDH, CPK, CEA, tryptophan, and polyamines, has not yet proved reliable enough for routine use.

It is known that tumor growth is associated with angiogenesis (the growth of new blood vessels), and it is believed that the mechanism for such tumor-induced angiogenesis is the secretion by tumors of one or more angiogenesis-promoting factors. Tumor-induced angiogenesis probably occurs as a result of first the migration of, followed by the proliferation of capillary endothelial cells.

A method for observing migration of cells, described in Albrecht-Buehler (1977), J. Cell Biol., 72, 595, involves plating cells onto glass coverslips which have been previously coated with gold particles. The cells ingest the gold and, as they move, leave bare areas or phagokinetic tracks as records of their movement. It has been observed, Ali et al. (1978), Cell, 14, 439, that an increased rate of cell movement is reflected in a longer phagokinetic track.

Because an increase in cell locomotion does not always correlate with an increase in directionality of movement, phagokinetic tracks are generally highly irregular, and track lengths are therefore very difficult to compare. The irregularity of the tracks would also render length an unreliable measure of movement, even if lengths could be measured.

I have now found that the phagokinetic tracks of capillary endothelial cells can be accurately quantified and compared using the area, rather than the length, as a measure. The track quantification serves as the basis for a non-invasive cancer diagnostic assay according to which a control and a test track which may appear to be of about the same length can be quantitatively compared to determine whether the test track area is larger, indicating a positive cancer diagnosis. The new assay is particularly useful for detecting cancers which secrete angiogenesis-promoting factors into human body fluids such as urine, aqueous humor, cerebrospinal fluid, seminal fluid, and sputum.

According to the cancer diagnostic assay of the invention, a substratum is provided which is coated with visible particles susceptible to ingestion by capillary endothelial cells. Onto that substratum are plated capillary endothelial cells which, after being allowed to adhere to the substratum, are incubated with the sample to be assayed (test sample). Following incubations, the area of the phagokinetic track left by at least one of the cells is measured and compared to the area of the track left by a control cell incubated under the same conditions, but in medium lacking test sample. A larger track area left by test cells indicates the presence in the test sample of a factor associated with cancer cells.

Because the assay is quantitative, it can be used to monitor the extensiveness of the disease in patients known to have cancer, as well as to diagnose new cases. The assay's quantitative accuracy also makes it useful for screening cancer chemotherapeutic agents for anti-migratory activity.

In preferred embodiments of the assay, bovine capillary endothelial cells are used to diagnose cancer using fluid derived from a patient; preferably, the assay detects bladder cancer by assaying urine. The preferred method of measuring track area involves fixing the cells and the track, projecting the track onto a television screen, tracing the projection onto a transparent surface, and automatically computing the track area on the surface using an electronic digital image analyzer. However, any track area measuring method can be used. For example, computerized scanning image analysis, although more expensive, provides high speed analysis of track size data.

Gold particles are the preferred substarate coating, but any visible, ingestible coating can be used, e.g., India ink or latex particles 1 to $3\mu$ in diameter. Any capillary endothelial cells, including human cells, can be used, although bovine cells are preferred because of their ready availability.

Because calls reproduce within about 24 hours, 18 hours is the preferred incubation time. I have found that, for an 18 hour incubation time, a test-track area increase of $5000\mu^2$ over the control track area is a reliable indication of a cancer-positive diagnosis.

The following specific examples are intended to more precisely point out the invention, without acting as limitations upon its scope.

EXAMPLE 1

Three thousand bovine capillary endothelial cells were seeded on gold particle-coated 22 mm×22 mm glass coverslips prepared according to the method of Albrecht-Buehler, Id. The cultures were then incubated at 37° C. in Dulbecco's modified Eagle's medium containing 10% calf serum (DME-CS) until the cells had attached to the coverslips (about 4 hours). The coverslips were then transferred to 35 mm culture dishes containing DME-CS alone, DME-CS mixed with 20%, 40%, 60%, 80% mouse sarcoma 180 cell extract, or pure mouse sarcoma 180 cell extract.

After an additional 18 hours of incubation, the medium was removed from each culture dish and replaced with 10% buffered formalin phosphate, to terminate the experiment and fix the cells and their tracks.

The images of the tracks were observed under incident light with a Nikon MS inverted microscope and then transferred to the screen of a Setchell-Carson 10M915 television by means of an RCA TC1005 video camera. The images were then traced from the television screen onto sheets of transparent plastic, which were subsequently placed onto the magnetic tablet of a Zeiss MOP-3 digital image analyzer. The tracings of the phagokinetic tracks were then retraced with the magnetic stylus of the MOP-3, and the dimensions of area, maximum diameter, and length of perimeter automatically computed.

To eliminate consideration of cell divisions and collisions, only tracks formed by a single cell were analyzed.

Figures 1, 2:
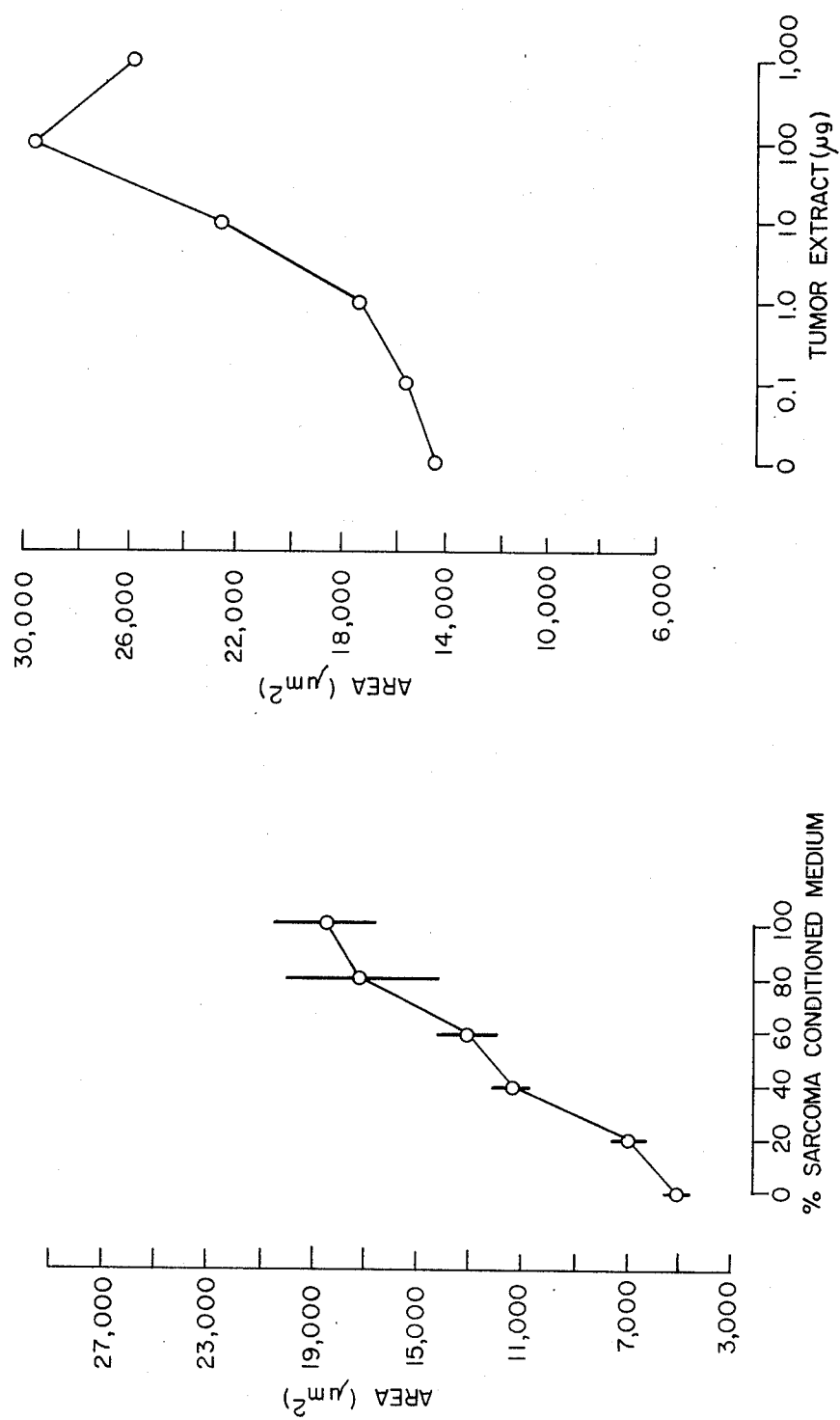
FIG. 1 is a graph of the relationship between track area and mouse sarcoma extract concentration in incubation medium.
FIG. 2 is a graph of the relationship between track area and human hepatoma extract concentration in incubation medium.

The results of the experiment are illustrated in the graph of FIG. 1, which shows the linear relationship between tumor extract concentration and track area.

EXAMPLE 2

A suspension of human hepatoma cells ($5 \times 10^7$ cells ml$^{-1}$) was incubated in phosphate-buffered saline for 4 hours at 4° C. The cells were removed by centrifugation and the resulting supernatant was concentrated and diluted in phosphate buffer (0.1 M NaH$_2$PO$_4$-0.02% NaN$_3$) four times to remove the saline.

The final concentrate was applied to a CM-Sephadex C-50 column equilibrated with the 0.1 M phosphate buffer. The material that eluted with the starting buffer was collected, pooled, dialyzed and lyophilized. Increasing concentrations of this material were added to 35-mm culture dishes containing 2 ml DME-CS. Gold-coated coverslips onto which 3,000 bovine capillary endothelial cells had been plated were transferred into these culture dishes and incubated for an additional 18 hours at 37° C. Areas of the phagokinetic tracks were determined as described in Example 1.

The graph of FIG. 2, in which each point represents the mean area of 100 samples±s.e.m., shows that track area increased with increased tumor extract concentrations up to 100 μg/ml.

EXAMPLE 3

The graphs of FIGS. 3-6 show the track areas of cells incubated with concentrated urine from four patients with histories of bladder cancer. Each area unit of 0.1 on the y axis of each graph represents an area of 1800μ$^2$.

Clear voided urine samples were collected from the four patients and frozen at −20° C. The samples were then thawed at room temperature and centrifuged at 1000 rpm. Forty to fifty cc of the supernatant were dialyzed against distilled water for 24 hours at 4° C. in Spectrapor dialysis tubing (cutoff=3500 MW). The samples were then centrifuged at 1000 rpm for 5 minutes and an aliquot tested for bacterial contamination using a Uricult dip slide.

The dialyzed samples were concentrated 10-fold in ultrafiltration apparatus and re-frozen at −20° C. until use.

The assays were carried out as described in Example 1, with the concentrated urine samples being used as the incubation media.

Figure 4:
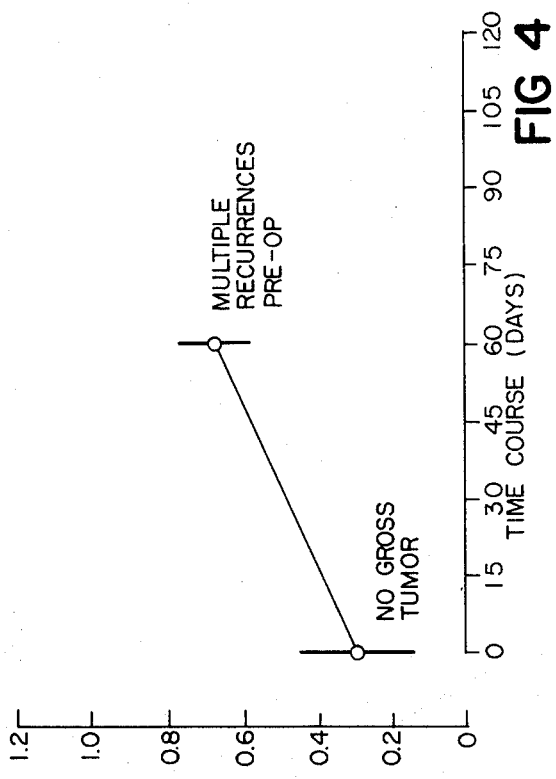
FIGS. 3-6 are graphs comparing the track areas of cells incubated with the urine of patients with and without detectable bladder cancer.
Figure 6:
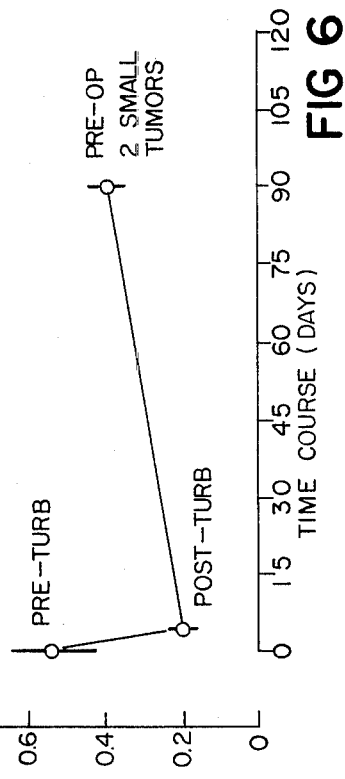
Figure 3:
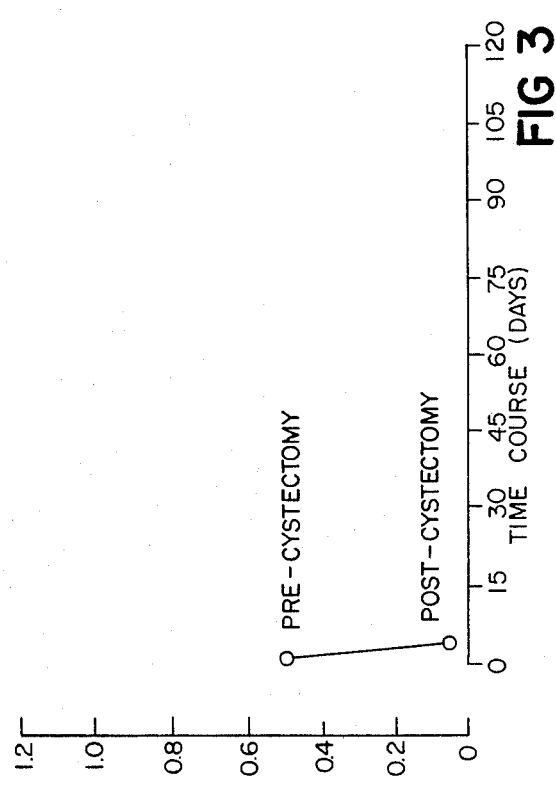
Figure 5:
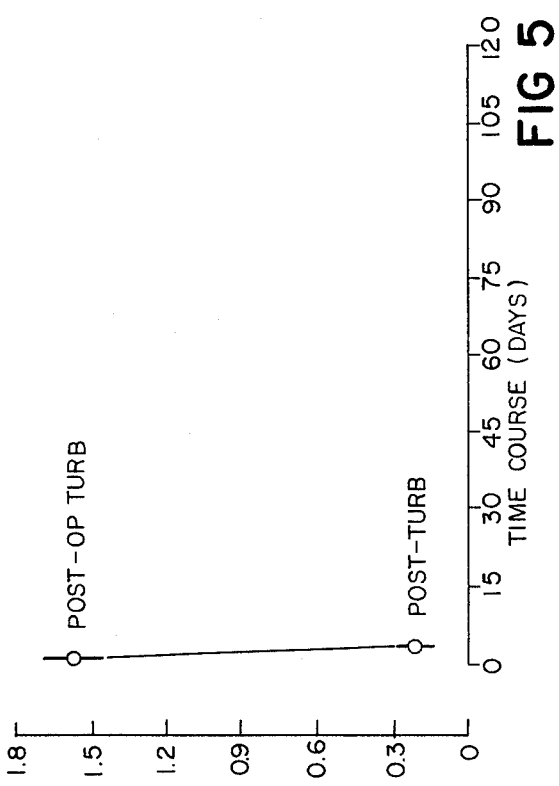

In FIGS. 3-6, the graphs show the correlation between increased track area and the presence of detectible bladder tumors. FIG. 3 illustrates the drop in track area observed for cells incubated with urine taken from a patient after surgical tumor removal. FIG. 4 shows the increase in track area correlated with tumor regrowth. FIG. 5 shows the drop in track area following surgical tumor removal, followed by an increase in area with tumor regrowth. FIG. 6 shows another post-operative area decrease.

What is claimed is:

1. An in vitro cancer diagnostic assay comprising
   providing a substratum coated with a layer of visible particles susceptible to ingestion by capillary endothelial cells,
   plating capillary endothelial cells onto said substratum,
   allowing said capillary endothelial cells to adhere to said substratum,
   incubating said adhered cells with medium comprising a test sample to be assayed for the presence of a factor associated with cancer cells,
   measuring the area of the visible particle-depleted phagokinetic track left by at least one of said capillary endothelial cells, and
   comparing said area with the phagokinetic track area left by at least one control capillary endothelial cell incubated under the same conditions, but in the absence of said test sample,
   a comparatively larger phagokinetic track area left by said cells incubated with said test sample indicating the presence in said test sample of said factor associated with cancer cells.

2. The assay of claim 1 wherein said capillary endothelial cells are of bovine origin.

3. The assay of claim 1 wherein said test sample comprises a fluid obtained from a human patient suspected of having cancer.

4. The assay of claim 3 wherein said fluid is urine and said cancer is bladder cancer.

5. The assay of claim 1 wherein said step of measuring said phagokinetic track area comprises
   fixing said cells and said track,
   projecting said track onto a television screen,
   tracing said projected track onto a transparent surface, and
   automatically computing said track area on said transparent surface using an electronic digital image analyzer.

6. The assay of claim 1 wherein
   said adhered cells are incubated with said medium comprising said test sample for about 18 hours, and
   a difference between control and test track areas of about 5000μ$^2$ indicates the presence in said test sample of said factor associated with cancer cells.

* * * * *